United States Patent
Kim et al.

(10) Patent No.: US 11,324,760 B2
(45) Date of Patent: May 10, 2022

(54) SOLID DISPERSION OF DUTASTERIDE, METHOD FOR PREPARING THE SOLID DISPERSION, AND PHARMACEUTICAL COMPOSITION INCLUDING THE SOLID DISPERSION

(71) Applicant: KOREA PRIME PHARM CO., LTD., Gwangju (KR)

(72) Inventors: Dae Ik Kim, Gwangju (KR); Woo Cheoul Shin, Suwon-si (KR)

(73) Assignee: KOREA PRIME PHARM CO., LTD., Gwangju-si (KR)

( * ) Notice: Subject to any disclaimer, the term of this patent is extended or adjusted under 35 U.S.C. 154(b) by 58 days.

(21) Appl. No.: 16/761,990

(22) PCT Filed: Nov. 12, 2018

(86) PCT No.: PCT/KR2018/013684
§ 371 (c)(1),
(2) Date: May 6, 2020

(87) PCT Pub. No.: WO2019/103373
PCT Pub. Date: May 31, 2019

(65) Prior Publication Data
US 2020/0306266 A1    Oct. 1, 2020

(30) Foreign Application Priority Data
Nov. 21, 2017 (KR) .................. 10-2017-0155985

(51) Int. Cl.
A61K 31/58     (2006.01)
A61K 47/02     (2006.01)
A61K 47/34     (2017.01)

(52) U.S. Cl.
CPC .............. *A61K 31/58* (2013.01); *A61K 47/02* (2013.01); *A61K 47/34* (2013.01)

(58) Field of Classification Search
CPC ......... A61K 47/02; A61K 9/143; A61K 9/146
See application file for complete search history.

(56) References Cited

U.S. PATENT DOCUMENTS

2006/0204588 A1    9/2006    Liversidge et al.
2008/0311162 A1    12/2008   Darmuzey et al.

FOREIGN PATENT DOCUMENTS

KR    10-0962447 B1    6/2010
KR    10-1055412 B1    8/2011
(Continued)

OTHER PUBLICATIONS

Kim et al, Investigation of Polymeric Excipients for Dutasteride Solid Dispersion and its PhysicoChemical Characterization, Arch. Pharm. Res. (Year: 2014).*
(Continued)

*Primary Examiner* — Carlos A Azpuru
(74) *Attorney, Agent, or Firm* — Novick, Kim & Lee, PLLC; Jae Youn Kim (57) ABSTRACT

A solid dispersion of dutasteride for improving the solubility or dissolution rate of poorly soluble dutasteride, a method for preparing the solid dispersion, and a pharmaceutical composition including the solid dispersion are provided. The solid dispersion includes: a coprecipitate including dutasteride and a water-soluble polymeric carrier; and an adsorbent. The dutasteride and the water-soluble polymeric carrier are present in a weight ratio of 1:10-100 in the coprecipitate.

7 Claims, 6 Drawing Sheets

(56) References Cited

FOREIGN PATENT DOCUMENTS

| KR | 10-2016-0087658 A | 7/2016 |
|----|-------------------|--------|
| KR | 10-1897995 B1 | 9/2018 |

OTHER PUBLICATIONS

Nam Ah Kim et al.,"Investigation of polymeric excipients for dutasteride solid dispersion and its physicochemical characterization", Article in Archives of Pharmacal Research, 2014, pp. 214-224, vol. 37.

D.V.Subba Rao et al., "Stress Degradation Studies on Dutasteride and Development of a Stability-Indicating HPLC Assay Method for Bulk Drug and Pharmaceutical Dosage Form", Research, Apr. 17, 2008, pp. 841-845, vol. 67.

\* cited by examiner

SOLID DISPERSION OF DUTASTERIDE, METHOD FOR PREPARING THE SOLID DISPERSION, AND PHARMACEUTICAL COMPOSITION INCLUDING THE SOLID DISPERSION

TECHNICAL FIELD

The present invention relates to a solid dispersion of dutasteride for improving the solubility or dissolution rate of poorly soluble dutasteride, a method for preparing the solid dispersion, and a pharmaceutical composition including the solid dispersion.

BACKGROUND ART

Dutasteride has the chemical name 17β-N-[2,5-bis(trifluoromethyl)]phenylcarbamoyl-4-aza-5α-androst-1-en-3-one represented by Formula I:

[Formula I]

Dutasteride inhibits the activity of 5α-reductase that converts testosterone, a male sex hormone, to dihydrotestosterone, a causative agent of androgenetic alopecia and benign prostatic hyperplasia. Due to this ability, dutasteride is used to treat benign prostatic hyperplasia and androgenetic alopecia.

Dutasteride is a poorly soluble drug that has a solubility of only 0.038 ng/mL in water and is relatively unstable enough to be degraded by oxidation and hydrolysis (Subba Rao & Radhakrishnanand, Chromatopia 67, 841-845 (2008)).

Thus, dutasteride is formulated into liquid preparations to increase its dissolution rate or is produced and commercially available in the form of soft capsules containing a stabilizer for its stabilization.

A representative commercially available product for dutasteride is AVODART® (Glaxosmithkline), which is an original branded product.

AVODART® is a pharmaceutical drug in which dutasteride is stabilized and is simultaneously solubilized such that it can be absorbed from the gastrointestinal tract when administered orally. Commercially available AVODART® capsules are produced by dissolving 0.5 mg of dutasteride and 0.035 mg of butylated hydroxytoluene as a stabilizer against oxidation and hydrolysis in 349.5 mg of oily capric acid/caprylic acid mono/diglyceride and filling the solution in soft gelatin capsules (AVODART®, FDA chemistry review).

However, such soft capsule preparations such as AVODART® capsules have their inherent problems.

That is, the properties and shape of the soft capsule preparations deteriorate because the capsules tend to soften or harden during storage due to the sensitivity of the main component gelatin to heat and moisture. Further, the gelatin may be crosslinked as a result of the reaction between the internal components and the capsules, resulting in delayed disintegration or dissolution. The addition of stabilizers such as butylated hydroxytoluene is required to enhance the stability of liquid preparations in view of the characteristics of the liquid preparations. However, butylated hydroxytoluene was reported to cause cancer, asthma, and behavior disorders of childhood.

In efforts to overcome the disadvantages of AVODART® soft capsules, a great deal of research has been conducted to formulate dutasteride into solid preparations. Some representative examples of the prior art were introduced in the following publications, which are incorporated herein by reference in their entirety.

Korean Patent Publication No. 2016-0087658 ("Patent Document 1") discloses a pharmaceutical composition that is prepared by dissolving dutasteride in a solubilizing agent, suspending the solution in light anhydrous silicic acid, homogeneously emulsifying the suspension, mixing the emulsion with a disintegrant and a dispersant, and drying the mixture. However, the use of the solubilizing agent in the form of an oily liquid creates a heavy burden in digestion and uptake. Further, the content of the solubilizing agent in the solid preparation should be limited as small as possible; otherwise, the solid preparation is difficult to produce.

Korean Patent No. 10-1055412 ("Patent Publication 2") discloses a method for producing tablets including dissolving dutasteride, poloxamer as a surfactant, and propylene glycol monocaprylate as an oily solubilizing agent in ethanol and adsorbing the solution to an adsorbent composed of silicified microcrystalline cellulose and silicon dioxide. However, there is a possibility that the use of ethanol during processing for improving the solubility of the main ingredient changes the crystallinity of dutasteride, and as a result, the formation of related substances of dutasteride is accelerated, increasing the risk that the stability of the tablets may deteriorate.

Korean Patent No. 10-0962447 ("Patent Document 3") discloses a self-emulsifying composition for solubilizing dutasteride and a tablet produced from the self-emulsifying composition. However, the self-emulsifying composition inevitably uses a large amount of a surfactant such as poloxamer or sucrose ester to form a self-dispersing emulsion. The surfactant may cause problems such as gastrointestinal disorders upon taking the tablet.

PRIOR ART DOCUMENTS (Patent Document 1) Korean Patent Publication No. 2016-0087658 A (Jul. 22, 2016)
(Patent Document 2) Korean Patent No. 10-1055412 B1 (Aug. 2, 2011)
(Patent Document 3) Korean Patent No. 10-0962447 B1 (Jun. 3, 2010)

DETAILED DESCRIPTION OF THE INVENTION

Problems to be Solved by the Invention

Thus, the present inventors have endeavored to provide a dutasteride-containing solid preparation that exhibits a dissolution rate and a solubility equal to or higher than soft capsules and has better storage stability than soft capsules while avoiding the use an organic solvent such as ethanol and a stabilizer such as butylated hydroxytoluene, which are harmful to humans, and a method for producing the dutasteride-containing solid preparation.

Means for Solving the Problems

The present invention has been made in an effort to solve the problems of the prior art and provides a solid dispersion of dutasteride including: a coprecipitate including dutasteride and a water-soluble polymeric carrier; and an adsorbent, wherein the dutasteride and the water-soluble polymeric carrier are present in a weight ratio of 1:10-100 in the coprecipitate.

In the present invention, the water-soluble polymeric carrier is selected from polyethylene glycol, polyvinylpyrrolidone, polyvinyl alcohol, polyvinylpyrrolidone-polyvinyl acetate copolymers, polyvinyl alcohol-polyvinylpyrrolidone copolymers, hydroxypropyl methylcellulose, hydroxypropyl cellulose, and mixtures thereof.

In the present invention, the dutasteride and the adsorbent are present in a weight ratio of 1:20-80.

In the present invention, the adsorbent is selected from magnesium aluminum silicate, colloidal silicon dioxide, attapulgite, bentonite, kaolin, and mixtures thereof.

In the present invention, the solid dispersion further includes at least one plasticizer selected from D-α-tocopheryl polyethylene glycol 1000 succinate (TPGS), polyethylene glycol 400, citrate esters, and triacetin.

In the present invention, the solid dispersion further includes at least one surfactant selected from sodium lauryl sulfate, polyoxyethylene sorbitan fatty acid esters, transesterification products of natural vegetable oil triglycerides and polyalkylene polyols, polyoxyethylene fatty acid esters, sorbitan fatty acid esters, propylene glycol mono- and di-fatty acid esters, pharmaceutically acceptable $C_{1-5}$ alkyl or tetrahydrofurfuryl di- or partial-ethers of mono- or polyoxyalkanediols, polyoxyethylene fatty acid ethers, and polyoxyethylene-polyoxypropylene copolymers.

The present invention also provides a pharmaceutical composition for treating prostatic hyperplasia or androgenetic alopecia including the solid dispersion wherein the pharmaceutical composition includes dutasteride as a main active ingredient.

The present invention also provides a method for preparing a solid dispersion of dutasteride, including: heating a water-soluble polymer to a temperature equal to or higher than the melting point of the water-soluble polymer with stirring and adding dutasteride to the molten water-soluble polymer; cooling the mixture and adding an adsorbent thereto; and drying the resulting mixture.

In the present invention, the water-soluble polymer and the adsorbent are used in amounts of 10 to 100 parts by weight and 20 to 80 parts by weight, based on one part by weight of the dutasteride, respectively.

Effects of the Invention

The solid dispersion of the present invention exhibits a dissolution rate equal to or higher than AVODART® soft capsules and contains a minimal amount of related substances, achieving good storage stability.

BEST MODE FOR CARRYING OUT THE INVENTION

The present invention will now be described in detail.

The present invention provides a solid dispersion of dutasteride including: a coprecipitate including dutasteride and a water-soluble polymeric carrier; and an adsorbent, wherein the dutasteride and the water-soluble polymeric carrier are present in a weight ratio of 1:10-100 in the coprecipitate.

The dutasteride as a main active ingredient and the water-soluble polymeric carrier are uniformly dispersed and precipitated in the coprecipitate.

In the solid dispersion of the present invention, the coprecipitate is adsorbed to the adsorbent. This adsorption increases the wettability of the dutasteride to further enhance the solubility and dissolution rate of the dutasteride.

The kind and molecular weight of the water-soluble polymeric carrier, the crystallinity, solubility and recrystallization properties of the drug, the choice of a suitable surfactant, and the contents of constituents in the solid dispersion are important for effective preparation of the solid dispersion. In addition, the processing parameters associated with the porosity and wettability of the particles need to be appropriately adjusted. If the content of the drug exceeds the upper limit defined above, the drug is present in the form of a crystal, and as a result, it undergoes an insignificant change in solubility and is readily recrystallized, making it difficult to expect the desired effects of the solid dispersion. Meanwhile, if the content of the polymeric carrier exceeds the upper limit defined above, the solubility and dissolution rate of the drug increase but the amount of the water-soluble polymeric carrier other than the drug should be optimized such that the solid dispersion is formulated into preparations suitable for oral administration, which is a generally preferable route for drug administration. Since increases in the crystallinity and solubility of the drug may vary depending on how the solid dispersion is prepared, determination of a suitable method for preparing the solid dispersion is also important.

Particularly, the dutasteride and the water-soluble polymeric carrier are present in a weight ratio of 1:10-100 in the coprecipitate. Preferably, the water-soluble polymeric carrier is preferably present in an amount of 20 to 80 parts by weight, more preferably 30 to 70 parts by weight, based on one part by weight of the dutasteride, but the amounts of the dutasteride and the water-soluble polymeric carrier are not necessarily limited thereto. If the content of the water-soluble polymeric carrier is less than 10 parts by weight, based on one part by weight of the dutasteride, the dutasteride and the water-soluble polymeric carrier are not sufficiently coprecipitated, making it impossible to expect enhanced solubility and dissolution rate, and there is a risk that the dutasteride may not be stabilized. Meanwhile, if the content of the water-soluble polymeric carrier exceeds 100 parts by weight, based on one part by weight of the dutasteride, the formulation becomes excessively viscous, making it difficult to obtain the solid dispersion, the content of the solid dispersion increases, and there is a low possibility that the amount of additives such as an excipient may be controlled, with the result that it is difficult to produce solid preparations such as tablets and the water-soluble polymeric carrier aggregates and precipitates.

The water-soluble polymeric carrier is selected from polyethylene glycol, polyvinylpyrrolidone, polyvinyl alcohol, polyvinylpyrrolidone-polyvinyl acetate copolymers, polyvinyl alcohol-polyvinylpyrrolidone copolymers, hydroxypropyl methylcellulose, hydroxypropyl cellulose, and mixtures thereof. Polyethylene glycol or polyvinylpyrrolidone is preferred. Polyethylene glycol is more preferred.

Particularly, polyethylene glycol is classified into various types having different molecular weights, as shown in Table 1. The polyethylene glycol types shown in Table 1 have different viscosities and melting points, which can be considered by one skilled in the art who intends to prepare the coprecipitate. Particularly, the use of polyethylene glycol products in the range of PEG4000 to PEG6000 is preferred when the dissolution rate of dutasteride and the physical properties (including flowability and tabletability) of the solid preparation are taken into consideration. The use of PEG4000 is more preferred.

TABLE 1

| | Polyethylene glycol average molecular weight | | | | | | |
|---|---|---|---|---|---|---|---|
| | 1000 | 1500 | 4000 | 6000 | 8000 | 20000 | 30000 |
| Melting point (° C.) | 37-40 | 44-48 | 50-58 | 55-63 | 60-63 | 60-63 | 65-70 |

The formation of the coprecipitate is initiated by mixing the water-soluble polymeric carrier in a molten state with the active ingredient dutasteride. The water-soluble polymeric carrier is preheated to a temperature slightly higher than its melting temperature until it becomes a liquid that can be mixed with the active ingredient dutasteride with stirring. The coprecipitation is completed by cooling (including cooling to room temperature). As a result of the cooling, the coprecipitate becomes a semi-solid to solid. When the polyethylene glycol has a high molecular weight, it is preferred to heat the coprecipitate in the presence of a plasticizer. The heating in the presence of the plasticizer serves to reduce the melting temperature of the water-soluble polymeric carrier and is preferred in terms of uniform melting.

The coprecipitate composed of only the dutasteride and the water-soluble polymeric carrier is slightly viscous, making it rather difficult to produce into the solid dispersion in the form of a powder. The presence of the adsorbent enables the preparation of the solid dispersion into solid preparations. The adsorption of the coprecipitate to the adsorbent improves the flowability and tabletability of the solid dispersion, advantageously facilitating the production of the solid dispersion into tablets and the handling of the solid dispersion. Surprisingly, this adsorption is also effective in increasing the dissolution rate of the dutasteride. A material bound to an adsorbent generally tends to be released from the adsorbent at a constant rate depending on its concentration. Accordingly, it is exceptional that the use of the adsorbent in the present invention improves the dissolution of the dutasteride from the coprecipitate. This is estimated because the interaction between the coprecipitate particles is reduced, presumably due to the presence of the adsorbent, but its precise mechanism needs to be clarified.

The adsorbent is selected from magnesium aluminum silicate (including magnesium aluminometasilicate, silicon dioxide (including colloidal silicon dioxide), attapulgite, microcrystalline cellulose, lactose, bentonite, kaolin, and mixtures thereof. Magnesium aluminometasilicate is preferred.

The adsorbent is present in an amount of 20 to 80 parts by weight, based on one part by weight of the dutasteride. If the adsorbent is present in an amount of less than 20 parts by weight, based on one part by weight of the dutasteride, the effect of binding the polymeric carrier to the adsorbent is negligible, and as a result, the influence of the adsorbent on improvements in flowability, tabletability, and dissolution rate is insufficient. Meanwhile, if the adsorbent is present in an amount exceeding 80 parts by weight, based on one part by weight of the dutasteride, the size of tablets increases excessively and there is a risk that the adsorbent may have a bad influence on the physical properties (such as dissolution rate) of the tablets.

The solid dispersion may further include a plasticizer. Any plasticizer that facilitates the melt molding of the water-soluble polymeric carrier may be used without limitation in the present invention. The plasticizer is preferably D-α-tocopheryl polyethylene glycol 1000 succinate (TPGS), polyethylene glycol 400, citrate esters, triacetin or a mixture thereof. Polyethylene glycol 400 is preferred. The plasticizer is used in an amount of 1 to 10% by weight, based on the total weight of the solid dispersion.

The solid dispersion can be prepared by a method including: heating the water-soluble polymer with stirring and adding dutasteride to the molten water-soluble polymer; cooling the mixture and adding the adsorbent thereto; and drying the resulting mixture. In a preferred embodiment, the solid dispersion includes 10 to 100 parts by weight of the water-soluble polymer and 20 to 80 parts by weight of the adsorbent, based on one part by weight of the dutasteride.

The solid dispersion of the present invention may be used without further purification as a medicament for oral administration. The solid dispersion may be formulated with at least one pharmaceutically acceptable excipient, disintegrant, binder, colorant, stabilizer, sweetener or lubricant to produce desired preparations such as powders, granules, capsules or tablets. Preferably, the solid dispersion is produced into film-coated tablets.

The present invention also provides a pharmaceutical composition for treating prostatic hyperplasia or androgenetic alopecia including the solid dispersion as an active ingredient.

The pharmaceutical composition of the present invention, together with one or more pharmaceutically acceptable carriers, may be formulated into suitable preparations. The pharmaceutical composition may further include an excipient or diluent. The term "pharmaceutically acceptable" means that the carriers are physiologically acceptable and cause no allergic reactions such as gastrointestinal disorders and dizziness or other similar reactions when administered to humans.

The pharmaceutical composition of the present invention may further include at least one surfactant selected from sodium lauryl sulfate, polyoxyethylene sorbitan fatty acid esters, transesterification products of natural vegetable oil triglycerides and polyalkylene polyols, polyoxyethylene fatty acid esters, sorbitan fatty acid esters, propylene glycol mono- and di-fatty acid esters, pharmaceutically acceptable $C_{1-5}$ alkyl or tetrahydrofurfuryl di- or partial-ethers of low molecular weight mono- or polyoxy-alkanediols, polyoxyethylene fatty acid ethers, and polyoxyethylene-polyoxypropylene copolymers. The surfactant is beneficial because of its ability to improve the dissolution rate and solubility of the poorly soluble dutasteride. However, the presence of an excess of the surfactant may cause gastrointestinal disorders. Thus, it is not recommended that an excess of the surfactant be administered. It is not necessary to use an excess of the surfactant because the dissolution and solubility of the solid dispersion are guaranteed in the present invention, unlike in the prior art. In view of this, the amount of the surfactant is preferably limited to at most 20% by weight, more preferably at most 15% by weight, even more preferably at most 10% by weight.

The pharmaceutically acceptable carrier may be, for example, a carrier for oral or parenteral administration.

Suitable carriers for oral administration include lactose, starch, cellulose derivatives, magnesium stearate, and stearic acid.

The pharmaceutical composition of the present invention may further include one or more additives such as lubricating agents, wetting agents, sweetening agents, flavoring agents, emulsifying agents, and suspending agents. Other pharmaceutically acceptable carriers and formulations can be found in Remington's Pharmaceutical Sciences, 19th ed., Mack Publishing Company, Easton, Pa., 1995.

The composition of the present invention may be administered to mammals, including humans, via various routes. For example, the composition of the present invention may be administered by orally or parenterally. For parenteral administration, it may be administered intravenously, intramuscularly, intraarterially, intramarrowly, intradurally, intracardiacally, transdermally, subcutaneously, intraperitoneally, intranasally, gastrointestinally, locally, sublingually or rectally.

The pharmaceutical composition of the present invention may be formulated into preparations for oral or parenteral administration depending on the route of administration described above.

The pharmaceutical composition of the present invention may be formulated into preparations for oral administration, such as powders, granules, tablets, pills, dragees, capsules, solutions, gels, syrups, slurries, and suspensions, by suitable methods known in the art. For example, the oral preparations may be tablets or dragees. In this case, the tablets or dragees may be produced by blending the active ingredient with a solid excipient, pulverizing the blend, adding a suitable aid to the powder, and granulating the mixture. Examples of suitable excipients include: sugars such as lactose, dextrose, sucrose, sorbitol, mannitol, xylitol, erythritol, and maltitol; starches such as corn starch, wheat starch, rice starch, and potato starch; celluloses such as cellulose, methyl cellulose, sodium carboxymethylcellulose, and hydroxypropyl methylcellulose; and fillers such as gelatin and polyvinylpyrrolidone. The pharmaceutical composition of the present invention may optionally further include a disintegrant, for example, crosslinked polyvinylpyrrolidone, agar, alginic acid or sodium alginate.

The pharmaceutical composition of the present invention may further include one or more additives selected from anticoagulants, lubricants, wetting agents, flavors, and preservatives.

The pharmaceutical composition of the present invention may be formulated into preparations for parenteral administration, such as injectable preparations, creams, lotions, ointments for external application, humectants, gels, aerosols, and nasal inhalers. These formulations are described in Remington's Pharmaceutical Science, 19th ed., Mack Publishing Company, Easton, Pa., 1995, which is a guidebook generally known in all pharmaceutical chemistry fields.

MODE FOR CARRYING OUT THE INVENTION

The present invention will be explained in more detail with reference to the following examples. However, it is noted that these examples are provided for illustrative purposes only and are not intended to limit the scope of the present invention.

EXAMPLES

Film-coated tablets having the compositions shown in Tables 2 and 3 were produced by the following basic procedure.

Procedure

The water-soluble polymeric carrier and the plasticizer were dissolved at 70-80° C. and dutasteride was added thereto. The mixture was stirred to obtain a homogeneous suspension. The suspension was cooled to room temperature and the adsorbent was added thereto. The resulting mixture was stirred to obtain a homogeneous solid dispersion (Optionally, the solid dispersion was dried and pulverized). To the solid dispersion were added the excipient, the disintegrant, and the surfactant. The mixture was homogenized, the lubricant was added thereto, followed by mixing and compression into uncoated tablets.

TABLE 2

| Components | | Example 1 | Example 2 | Example 3 | Example 4 | Example 5 | Example 6 |
|---|---|---|---|---|---|---|---|
| Main ingredient | Dutasteride | 0.5 | 0.5 | 0.5 | 0.5 | 0.5 | 0.5 |
| Polymeric carriers | PEG4000 | 20.0 | 20.0 | — | 30.0 | 30.0 | 30.0 |
| | PEG30000 | — | — | — | — | — | — |
| Plasticizers | PEG400 | 5.5 | 5.5 | — | 5.5 | 5.5 | 5.5 |
| | HPC-L (4000) | — | — | 0.5 | — | — | — |
| Adsorbents | Syloid XDP3150 | 20.0 | 20.0 | — | 20.0 | 20.0 | 20.0 |
| | Magnesium aluminum silicate | — | — | — | — | — | — |
| Excipients | MCC102 | 52.0 | 50.0 | 62.0 | 30.0 | 15.0 | 15.0 |
| | Mannitol | — | — | — | 22.0 | 17.0 | 17.0 |
| | Prosolv SMCC 90 | — | — | — | — | — | — |
| | Anhydrous lactose | — | — | — | 30.0 | 15.0 | 15.0 |
| | Lactose D | — | — | 45 | — | — | — |
| Disintegrants | Crospovidone | 30.0 | 40.0 | 25.0 | 5.0 | 40.0 | 40.0 |
| | Sodium starch glycolate | 10.0 | 20.0 | — | — | — | — |
| Surfactant | SLS | 15.0 | 15.0 | — | 10.0 | 10.0 | 10.0 |
| Lubricants | Magnesium stearate | 2.0 | 2.0 | 2.0 | 2.0 | 2.0 | 2.0 |
| | Colloidal silicon dioxide | — | — | — | — | — | 3.0 |
| | Total weight | 155.0 | 173.0 | 135.0 | 155.0 | 155.0 | 158.0 |

TABLE 3

| Components | | Example 7 | Example 8 | Example 9 | Example 10 | Example 11 | Example 12 |
|---|---|---|---|---|---|---|---|
| Main ingredient | Dutasteride | 0.5 | 0.5 | 0.5 | 0.5 | 0.5 | 0.5 |
| Polymeric carriers | PEG4000 | 30.0 | 30.0 | 30.0 | 30.0 | 30.0 | — |
| | PEG30000 | — | — | — | — | — | 30.0 |
| Plasticizers | PEG400 | 5.5 | 5.5 | 5.5 | 5.5 | 5.5 | 5.5 |
| | HPC-L (4000) | — | — | — | — | — | — |
| Adsorbents | Syloid XDP3150 | 20.0 | 20.0 | — | — | — | — |
| | Magnesium aluminum silicate | — | — | 20.0 | 20.0 | — | 20.0 |
| Excipients | MCC102 | 50.0 | — | 15.0 | — | 15.0 | — |
| | Mannitol | — | — | 17.0 | — | — | — |
| | Prosolv SMCC 90 | — | 32.0 | — | 32.0 | 32.0 | 32.0 |
| | Anhydrous lactose | 15.0 | 15.0 | 15.0 | 15.0 | 15.0 | 15.0 |
| | Lactose D | — | — | — | — | — | — |
| Disintegrants | Crospovidone | 40.0 | 40.0 | 40.0 | 40.0 | 40.0 | 40.0 |
| | Sodium starch glycolate | — | — | — | — | — | — |
| Surfactant | SLS | 10.0 | 10.0 | 10.0 | 10.0 | 10.0 | 10.0 |
| Lubricants | Magnesium stearate | 2.0 | 2.0 | 2.0 | 2.0 | 2.0 | 2.0 |
| | Colloidal silicon dioxide | — | 3.0 | — | — | — | — |
| | Total weight | 173.0 | 155.0 | 158.0 | 155.0 | 150.0 | 155.0 |

Example 13

A solution of Opadry Blue (03F40519) in 5.58 mg of purified water and 22.32 mg of ethanol as solvents was coated on the uncoated tablets of Example 10 to produce film-coated tablets.

Evaluation of Characteristics of the Preparations

The hardness and friability of the preparations were measured using a hardness tester (KTF-25, International Engineering) and a friability tester (3880, KIYA SEISAKUSHO). The preparation was judged to have good tabletability when the friability was ≤0.5%, the angle of repose indicating its flowability was ≤45°, and the CI value was ≤30%.

Evaluation of Dissolution Rates

[Dissolution Test Conditions]

Dissolution test conditions specified in the standard and test method (0.1 N HCl, 2.0% SLS) were applied to AVODART® soft capsules as reference preparations. Dissolution test conditions specified in the standard and test method or modified pharmaceutical equivalence test conditions (0.3% SLS) were applied to the preparations of Examples 1-12.

The characteristics of the preparations of Examples 1-12 are summarized in Table 4. The dissolution rates from the preparations are shown in FIGS. 1 to 6.

The hardness values of the preparations of Examples 1-8 were measured to be 2-4 kP, which are rather unsuitable for coating. The use of syloid resulted in poor flowability during tableting due to its bulkiness, causing a mass variation of 10%.

In contrast, the preparations of Examples 9 and 10 were highly flowable and had hardness values of 5-7 kP, demonstrating that the preparations cause no problems during coating.

The preparations of Examples 11 and 12 suffered from problems during kneading or could not be tableted due to their inability to pass through meshes after mixing.

Figure 1:
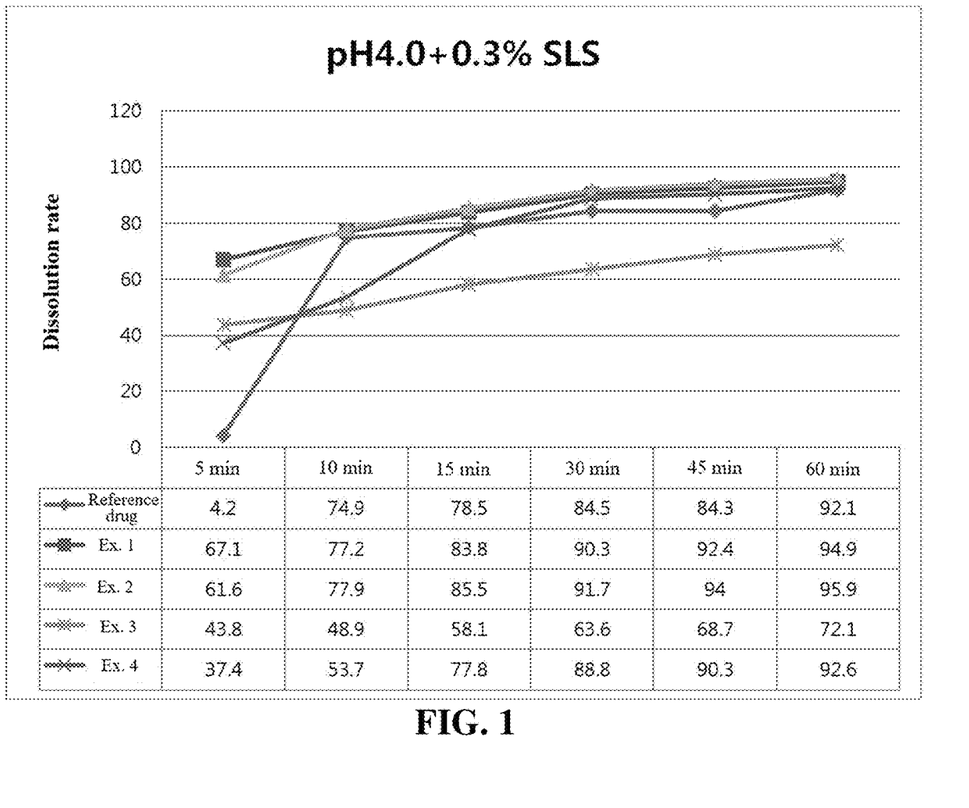
FIGS. 1 to 6 are graphs comparing the dissolution rates of dutasteride from preparations produced in Examples 1-13 and AVODART®.
Figure 2:
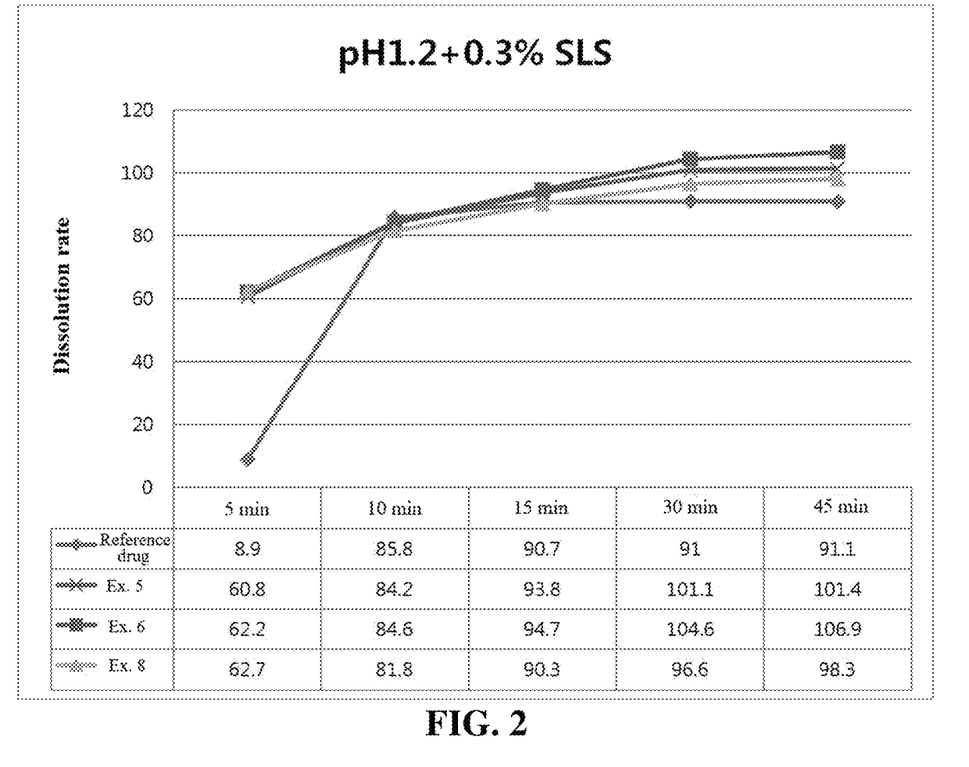
Figure 3:
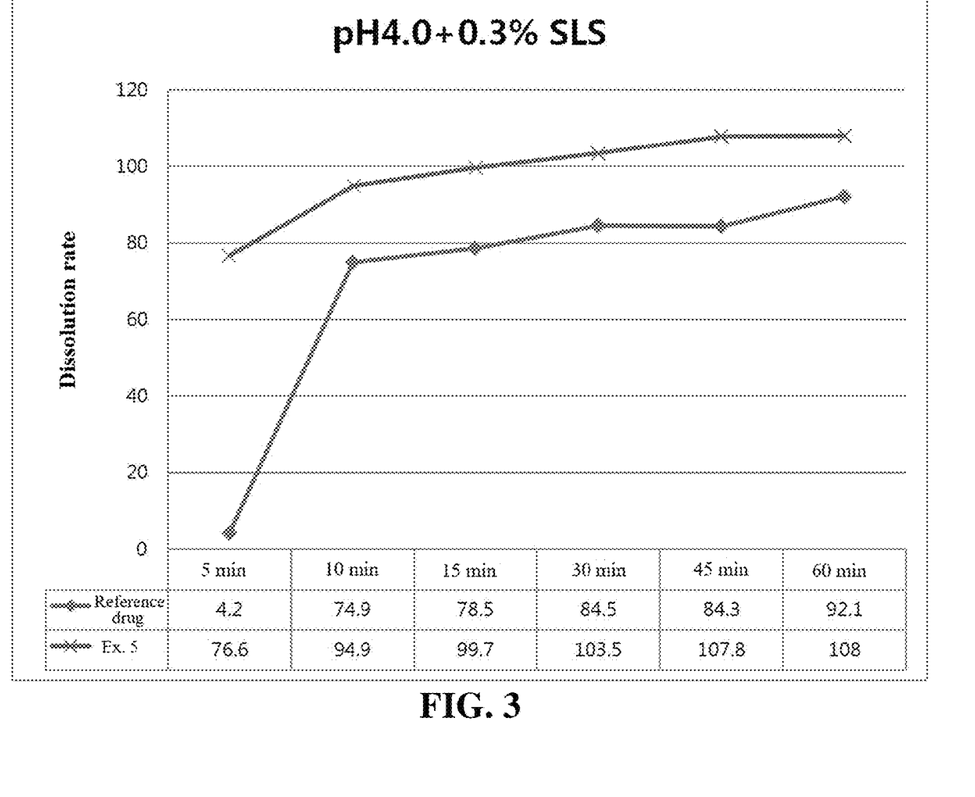
Figure 4:
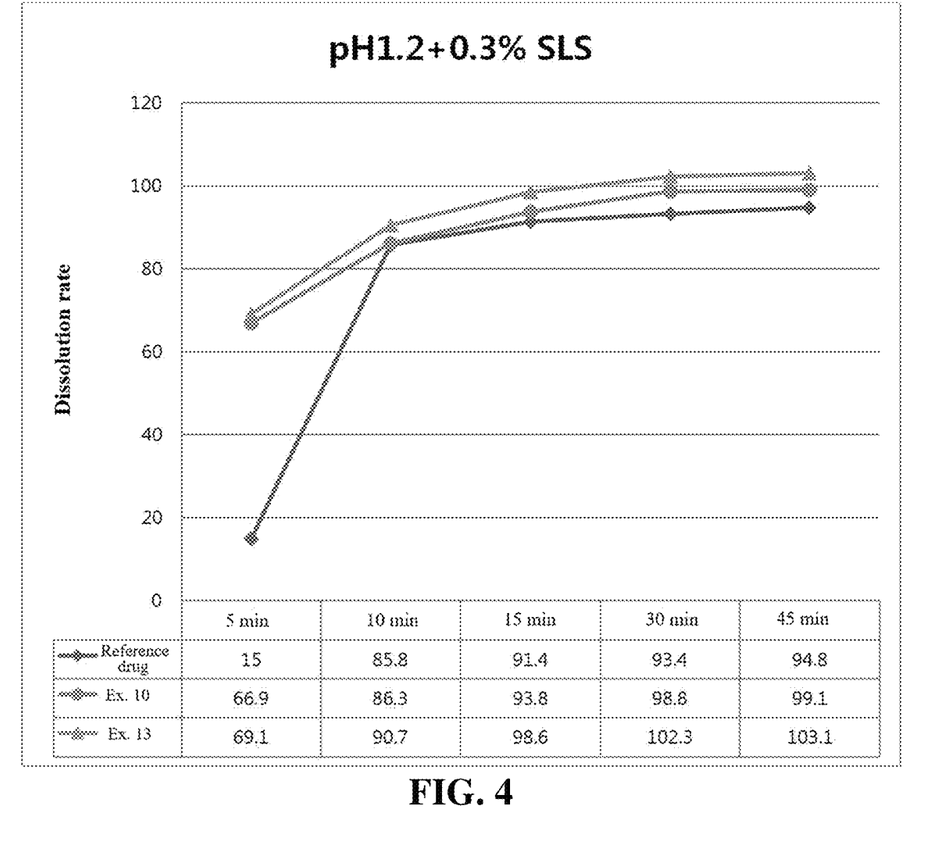
Figure 5:
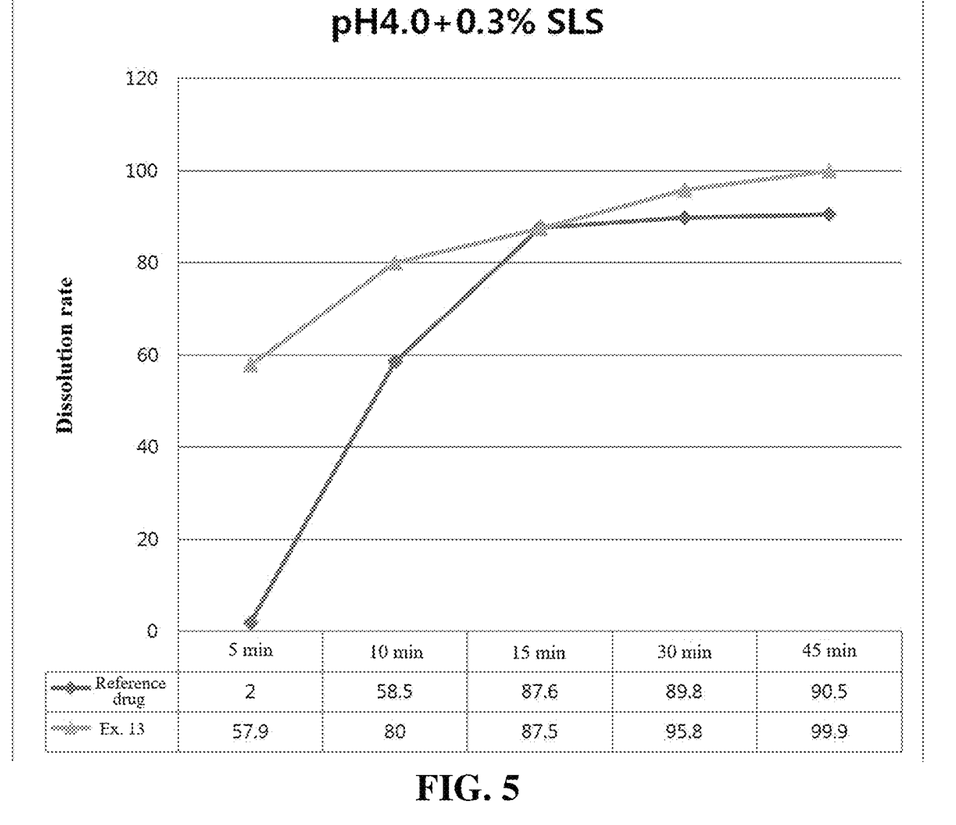
Figure 6:
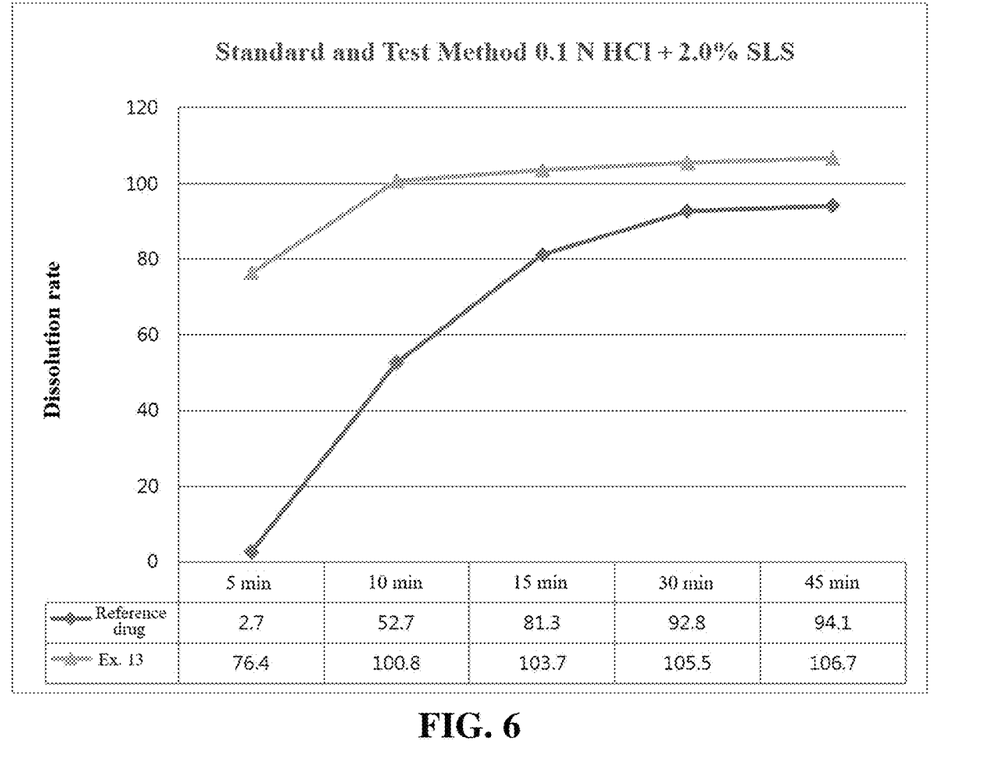

The dissolution rates of dutasteride from the preparations of Examples 1-10 were overall high. However, the preparations of Example 3 had a final dissolution rate in the early 70%, which was lower than that from the reference preparations. In contrast, the preparations of Example 13 had a dissolution rate of ≥80% after 45 min based on the standard and test method, as shown in FIG. 6, and showed better dissolution properties overall than the reference preparations.

Evaluation of Storage Stability of the Preparations

The storage stabilities of the preparations were evaluated according to the test criteria for related substances. As shown in Table 5, the preparations caused no problems in storage stability.

TABLE 4

| | Example No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Friability | good | good | good | good | good | good | poor | good | good | good | Impossible to knead and compress | |
| Flowability | poor | poor | poor | poor | poor | poor | poor | poor | good | good | | |
| Tabletability | 4 kP | 4 kP | 4 kP | 4 kP | 4 kP | 4 kP | 4 kP | 4 kP | 5 kP | 9 kP | | |

TABLE 5

Related substance test 1/<Aug. 16, 2017>

| Reference | | Raw material | Initial | After 2 months under accelerated conditions | |
|---|---|---|---|---|---|
| | | | | HDPE bottle | PVDC |
| ≤0.2% | Related substance A | Not detected | Not detected | Not detected | Not detected |
| ≤0.15% | Related substance B | Not detected | ≤0.05% (0.003%) | Not detected | Not detected |
| ≤0.2% | Related substance C | ≤0.05% (0.011%) | 0.14% | 0.08% | 0.07% |
| ≤0.3% | Related substance E | Not detected | Not detected | ≤0.05% (0.01%) | Not detected |
| ≤0.4% | Related substance F | Not detected | Not detected | Not detected | Not detected |
| ≤0.3% | Related substance G | Not detected | ≤0.05% (0.02%) | ≤0.05% (0.01%) | Not detected |
| Unknown related substance ≤0.1% | Unknown related substance | ≤0.05% (0.009%) | ≤0.05% (0.004%) | ≤0.05% (0.01%) | ≤0.05% (0.004%) |
| Unknown related substance ≤0.1% | Unknown related substance | ≤0.05% (0.005%) | ≤0.05% (0.006%) | Not detected | ≤0.05% (0.01%) |
| Unknown related substance ≤0.1% | Unknown related substance | ≤0.05% (0.008%) | ≤0.05% (0.007%) | Not detected | ≤0.05% (0.005%) |
| Unknown related substance ≤0.1% | Unknown related substance | Not detected | ≤0.05% (0.003%) | Not detected | 0.096% |
| Unknown related substance ≤0.1% | Unknown related substance | Not detected | ≤0.05% (0.006%) | Not detected | ≤0.05% (0.007%) |
| Unknown related substance ≤0.1% | Unknown related substance | Not detected | Not detected | Not detected | ≤0.05% (0.006%) |
| Judgement | | Suitable | Suitable | Suitable | Suitable |

The invention claimed is:

1. A solid dispersion comprising:
a coprecipitate comprising dutasteride and a water-soluble polymeric carrier; and an adsorbent,
wherein the dutasteride and the water-soluble polymeric carrier are present in a weight ratio of 1:10-100 in the coprecipitate.

2. The solid dispersion according to claim 1, wherein the water-soluble polymeric carrier is selected from polyethylene glycol, polyvinylpyrrolidone, polyvinyl alcohol, polyvinylpyrrolidone-polyvinyl acetate copolymers, polyvinyl alcohol-polyvinylpyrrolidone copolymers, hydroxypropyl methylcellulose, hydroxypropyl cellulose, and mixtures thereof.

3. The solid dispersion according to claim 1, wherein the dutasteride and the adsorbent are present in a weight ratio of 1:20-80.

4. The solid dispersion according to claim 1, wherein the adsorbent is selected from magnesium aluminum silicate, colloidal silicon dioxide, attapulgite, bentonite, kaolin, and mixtures thereof.

5. The solid dispersion according to claim 1, further comprising at least one plasticizer selected from D-α-tocopheryl polyethylene glycol 1000 succinate (TPGS), polyethylene glycol 400, citrate esters, and triacetin.

6. The solid dispersion according to claim 1, further comprising at least one surfactant selected from sodium lauryl sulfate, polyoxyethylene sorbitan fatty acid esters, transesterification products of natural vegetable oil triglycerides and polyalkylene polyols, polyoxyethylene fatty acid esters, sorbitan fatty acid esters, propylene glycol mono- and di-fatty acid esters, pharmaceutically acceptable C1-5 alkyl or tetrahydrofurfuryl di- or partial-ethers of low molecular weight mono- or polyoxy-alkanediols, polyoxyethylene fatty acid ethers, and polyoxyethylene-polyoxypropylene copolymers.

7. A pharmaceutical composition for treating prostatic hyperplasia or androgenetic alopecia comprising the solid dispersion according to claim 1.

* * * * *